United States Patent [19]

Foguet et al.

[11] Patent Number: 5,736,558
[45] Date of Patent: Apr. 7, 1998

[54] 4-(6-FLUORO-1,2-BENZISOXAZOLYL)-1 PIPERIDINYL-PROPOXY-CHROMEN-4-ONE- ONE-DERIVATIVES, THEIR PREPARATION AND THEIR USE IN THE TREATMENT OF PSYCHOSIS, SCHIZOPHRENIA AND ANXIETY

[75] Inventors: Rafael Foguet; Lluis Anglada; Jordi Bolos; Aurelio Sacristan; Josep M. Castello; Jose A. Ortiz, all of Barcelona, Spain

[73] Assignee: Ferrer Internacional, S.A., Barcelona, Spain

[21] Appl. No.: 750,790

[22] PCT Filed: Apr. 11, 1996

[86] PCT No.: PCT/EP96/01551

§ 371 Date: Mar. 14, 1997

§ 102(e) Date: Mar. 14, 1997

[87] PCT Pub. No.: WO96/32389

PCT Pub. Date: Oct. 17, 1996

[30] Foreign Application Priority Data

Apr. 12, 1995 [ES] Spain .................................. 9500737
Feb. 9, 1996 [ES] Spain .................................. 9600323

[51] Int. Cl.$^6$ ........................ A61K 31/445; C07D 401/14
[52] U.S. Cl. ............................................ 514/321; 546/198
[58] Field of Search ............................. 546/198; 514/321

[56] References Cited

U.S. PATENT DOCUMENTS 4,678,787  7/1987  Jaen ........................................ 514/253
5,100,902  3/1992  Peglion ................................... 514/321

OTHER PUBLICATIONS

McMillen et al., Drug Dev. Res. 12, 53–62 (1988).

Jaen et al., J. Med. Chem. 34, 248–256 (1991).

*Primary Examiner*—C. Warren Ivy
*Assistant Examiner*—Evelyn Huang
*Attorney, Agent, or Firm*—Birch, Stewart, Kolasch & Birch, LLP

[57] ABSTRACT

The present invention relates to 4-(6-fluoro-1,2-benzisoxazolyl)-1-piperidinyl-propoxy-chromen-4-one derivatives having the formula (I):

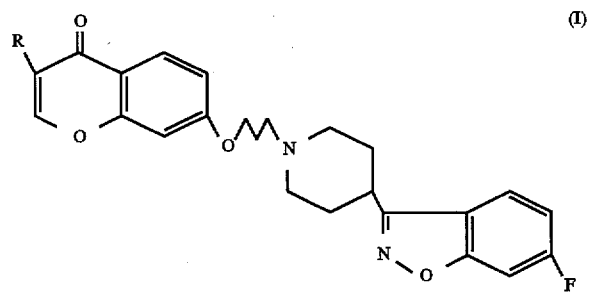

wherein R is hydrogen or alkyl having 1 to 4 carbon atoms optionally substituted by hydroxyl, as well as their pharmaceutically acceptable addition salts, which are useful in the treatment of psychosis, schizophrenia and anxiety.

7 Claims, No Drawings

4-(6-FLUORO-1,2-BENZISOXAZOLYL)-1 PIPERIDINYL-PROPOXY-CHROMEN-4-ONE-ONE-DERIVATIVES, THEIR PREPARATION AND THEIR USE IN THE TREATMENT OF PSYCHOSIS, SCHIZOPHRENIA AND ANXIETY

This application is the national phase of PCT/EP96/01551 filed on Apr. 11, 1996.

The present invention relates to new 4-(6-fluoro-1,2-benzisoxazolyl)-1-piperidinyl-propoxy-chromen-4-one derivatives having the formula (I):

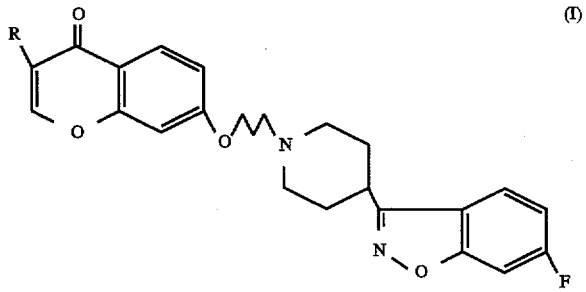

wherein R is hydrogen or alkyl having 1 to 4 carbon atoms optionally substituted by hydroxyl, as well as its pharmaceutically acceptable addition salts.

The compounds of the present invention, namely, 7-[3-[4-(6-fluoro-1,2-benzisoxazole-3-yl)piperidin-1-yl]propoxy]chromen-4-one, 7-[3-[4-(6-fluoro-1,2-benzisoxazole-3-yl) piperidin-1-yl]propoxy]-3-methyl-chromen-4-one and 7-[3-[4-(6-fluoro-1,2-benzisoxazole-3-yl)piperidin-1-yl]propoxy]-3-(hydroxymethyl)-chromen-4-one, are obtained by reacting 7-(3-halopropoxy)-4H-1-benzopyran-4-ones of general formula (II), wherein R is as defined for (I) and X is chlorine or bromine, with 6-fluoro-3-(4-piperidinyl)-1,2-benzisoxazole (III), according to Scheme 1, in the presence of a base selected between an alkali or earth-alkali metal carbonate or acid carbonate and a catalytic quantity of potassium iodide. The reaction occurs conveniently under heating and in a nonpolar medium, such as that composed of a solvent selected from N,N-dimethylformamide, acetonitrile or the like. From compounds (I), their pharmaceutically acceptable addition salts may be obtained by adding the proper acids according to conventional methods of Organic Chemistry.

Spanish Patent No. 9400581 describes the obtention of 7-[3-(4-p-fluorobenzoyl-1-piperidinyl)propoxy]chromen-4-one hydrochloride and its use as a neuroleptic.

The compounds of formula (I) are different from the compound in Spanish Patent No. 9400581 and are not obvious from the disclosure of such a patent. The compounds of the present invention also show an interesting profile as neuroleptics; the applicants have found out that their therapeutic index is surprisingly higher than that of its preceding one. This provides a larger safety for their therapeutic use and, in addition, a higher affinity to $5HT_{1a}$-receptors, which also makes them to be potentially useful in the treatment of anxiety.

Biochemical assays have revealed that the compounds of formula (I) exhibit an enhanced action on the receptors involved in neuroleptic ($D_2$ and $5HT_2$) and anxiolytic ($5HT_{1a}$) actions (B. A. McMillen et al., "Drug Dev. Res.", 1988, 12, 53–62).

Specific binding to $D_2$, $5HT_2$ and, $5HT_{1a}$ receptors was tested as follows:

$D_2$ receptors: A 2-nM solution of radioactive spiperone ([$^3$H]spiperone), which acts as a specific ligand, was incubated with the membrane corresponding to 20 mg of rat striatum for 20 min at 35° C. buffered at pH 7.4 with Tris.HCl. The non-specific binding was then determined by addition of a micromolar concentration of unlabelled spiperone. $IC_{50}$ (inhibitory concentration 50%) was calculated from the inhibition rate of the specific binding obtained by addition of eleven different concentrations of the compounds to be tested. After the incubation was completed, the sample was filtered through a glass fiber filter and then washed three times with Tris.HCl buffer. The amount of receptor-bound radioactivity was retained on the membrane and determined by liquid scintillation counting.

$5HT_2$ receptors: A 0.5 nM solution of radioactive ketanserin ([$^3$H]ketanserin, which acts as a specific ligand, was incubated with the membrane corresponding to 1 mg of rat cortex for 30 min at 35° C. buffered at pH 7.4 with Tris.HCl. Non-specific binding was then determined by addition of 5 micromolar concentration of unlabelled mianserin. $IC_{50}$ (inhibitory concentration 50%) was calculated from the inhibition rate of the specific binding obtained by addition of eleven different concentrations of the compounds to be tested. After the incubation was completed, the sample was filtered through a glass fiber filter and then washed three times with Tris.HCl buffer. The amount of receptor-bound radioactivity was retained on the membrane and determined by liquid scintillation counting.

Scheme 1

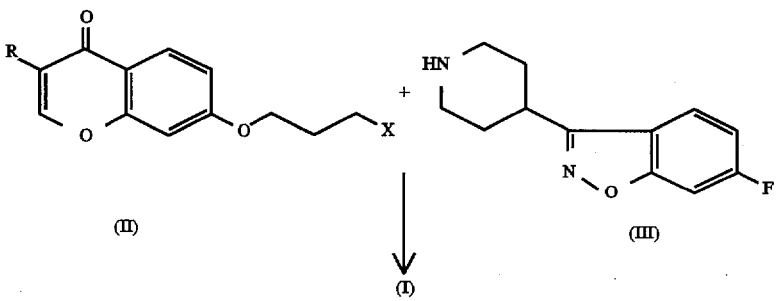

The starting compounds of the general formula (II) may be obtained by known procedures of Organic Chemistry as described in "J.Med.Chem.", 34, 248–256, 1991 and in previous patents of addition, ES 9401437 and ES 9500163.

$5HT_{1a}$ receptors: A 1 nM solution of radioactive 5-OH-DPAT ([$^3$H]5-OH-DPAT), which acts as a specific ligand, was incubated with the membrane corresponding to 1 mg of rat cortex for 20 min at 35° C. buffered at pH 7.4 with Tris.HCl.

Non-specific binding was then determined by addition of a 20 micromolar concentration of unlabelled buspirone. $IC_{50}$ (inhibitory concentration 50%) was calculated from the inhibition rate of the specific binding obtained by addition of eleven different concentrations of the compounds to be tested. After the incubation was completed, the sample was filtered through a glass fiber filter and then washed three times with Tris.HCl buffer. The amount of receptor-bound radioactivity was retained on the membrane and determined by liquid scintillation counting.

The biochemical results expressed as $IC_{50}$ in molar concentrations are presented in Table 1 comparatively to the compound of Patent ES 9400581. A higher affinity of the present compounds to the three receptors is observed.

TABLE 1

| | $IC_{50}$ | | | |
|---|---|---|---|---|
| | Ex. 1 | Ex. 2 | Ex. 3 | ES 9400581 (Ex. 1) |
| $D_2$ | $3.0 \times 10^{-8}$ | $1.66 \times 10^{-8}$ | $1.16 \times 10^{-8}$ | $4.36 \times 10^{-7}$ |
| $5HT_2$ | $1.12 \times 10^{-8}$ | $1.13 \times 10^{-8}$ | $4.71 \times 10^{-9}$ | $1.71 \times 10^{-8}$ |
| $5HT_{1a}$ | $3.83 \times 10^{-7}$ | $2.49 \times 10^{-7}$ | $1.52 \times 10^{-7}$ | $1.56 \times 10^{-6}$ |

The compounds were compared in Animal Pharmacology by the inhibition test of apomorphine-induced climbing behaviour (P.Protais et al: "Psychopharmacology", 50, 1–6, 1976). For the practical performance of this experiment, male Swiss mice weighing 22–24 g were used. One week prior to experiment, animals were kept in our facilities at a temperature of 20°–22° C. and 12/12 h light-dark cycle, and had free access to food and water. Two hours prior to experiment, the animals were placed in individual cages without access to food.

Animals were administered orally with test drug or 0.25% agar at time 0. After 60 minutes, apomorphine was subcutaneously injected at a dose of 1 mg/kg, and after further 70 minutes the animal's behaviour was assessed. Two additional assessments were performed at 10-min intervals.

For assessment, each animal was placed on the bottom of a small upright box (11×7.5×4.5 cm). The walls of the box were made of translucent methacrylate except one of the lateral surfaces (7.5 cm wide) which was a 3-mm wire mesh. The position of the animal was scored for 2 minutes according to the following criteria: 0=four paws on the floor; 1=three paws on the floor; 2=two paws on the floor; 3=one paw on the floor; and 4=four paws holding the wire mesh. If an animal keeps several positions within the 2-min observation, the seconds elapsed in each position will be recorded. Finally, mean scoring was calculated. Under these experimental conditions, the inhibitory doses 50% ($ID_{50}$) of the compounds are expressed in mg/kg in Table 2.

TABLE 2

| | $ID_{50}$ | | | |
|---|---|---|---|---|
| | Ex. 1 | Ex. 2 | Ex. 3 | ES 9400581 (Ex.1) |
| Climbing | 2.7 | 0.4 | 0.25 | 6.4 |

This experiment demonstrates that the compounds of the present invention are at least twice more potent as neuroleptics than the compound of Example 1 in Patent ES 9400581.

The activity of the compounds of the present invention was determined in the catalepsy test. The results, expressed as $ED_{50}$ in mg/kg by the oral route in rats, along with their therapeutic index (TI) versus the $ID_{50}$ values determined in the apomorphine-induced climbing behaviour test are presented in Table 3.

TABLE 3

| | $ED_{50}$ | | | |
|---|---|---|---|---|
| | Ex. 1 | Ex. 2 | Ex. 3 | ES 9400581 (Ex.1) |
| Catalepsy | 11.25 | 2.9 | 3.8 | 22.5 |
| TI($ED_{50}/ID_{50}$) | 4.17 | 7.25 | 15.2 | 3.52 |

Therefore, the therapeutic index (TI) of the compounds of the present invention is higher than that of the compound of Example 1 in Patent ES 9400581.

Example 1

7-[3-[4-(6-fluoro-1,2-benzisoxazole-3-yl) piperidin-1-yl] propoxy]chromen-4-one 2 g (8.4 moles) de 7-(3-chloropropoxy)-4H-1-benzopyran-4-one, 2.15 g (8.4 mmoles) of 6-fluoro-3-(4-piperidinyl)-1,2-benzisoxazole (European Patent 196132), 4.64 g (33.6 mmoles) of potassium carbonate and a catalytic amount of potassium iodide were suspended in 40 ml of N,N-dimethyl-formamide. The reaction mixture was heated for 18 hours at a temperature ranging between 85° and 90° C., then cooled to 20° C. and poured onto a mixture containing 100 ml of water and 100 ml of dichloromethane. The organic phase was washed with 5×50 ml of water, dried and the solvent was removed by distillation at reduced pressure. The solid obtained was purified on a silica gel column using acetonitrile/methanol as eluent. 1.5 g of chromatographically pure product were obtained. By recrystallization from methanol, 1.3 g of a yellowish-white solid were obtained which corresponded to 7-[3-[4-(6-fluoro-1,2-benzisoxazole-3-yl)piperidin-1-yl]propoxy]chromen-4-one, mp 132.5°–133.8° C.

$H^1$-NMR (CDCl$_3$): δ=2.04–2.19, m, 8H; 2.6, t, 2H; 3.07–3.11, m, 3 H; 4.14, t, 2H; 6.27, d, 1H; 6.87, d, 1H; 6.95–6.99, dd, 1H; 7.02–7.08, dt, 1H; 7.22–7.25, dd, 1H; 7.67–7.71, dd, 1H; 7.78, d, 1H; 8.09, d, 1H.

IR (KBr): 1680, 1660, 1320, 1270, 820 cm$^{-1}$.

Example 2

7-[3-[4-(6-fluoro-1,2-benzisoxazole-3-yl) piperidin-1-yl] propoxy]-3-methyl-chromen-4-one A mixture of 0.90 g (3.56 mmoles) of 7-(3-chloropropoxy)-3-methyl-chromen-4-one, 0.91 g (3.54 mmoles) of 6-fluoro-3-(4-piperidinyl)-1,2-benzisoxazole hydrochloride, 1 g (7.24 mmoles) of anhydrous potassium carbonate and a catalytic amount of potassium iodide in 20 ml of acetonitrile was heated at reflux for 18 hours. The reaction crude product was allowed to cool at room temperature and then was poured onto a mixture containing 100 ml of water and 100 ml of chloroform. The organic phase was decanted, washed with two portions of 50 ml of water, dried over anhydrous sodium sulfate, filtered and evaporated to reduced pressure. The residue obtained was purified by crystallization in ethyl acetate to give 0.66 g of a solid that corresponded to 7-[3-[4-(6-fluoro-1,2-benzisoxazole-3-yl) piperidin-1-yl]propoxy]-3-methyl-chromen-4-one, mp 157°–158° C.

¹H-NMR (CDCl₃): δ=2.01 (s, 3H, CH₃); 2.05–2.25 (m, 8H); 2.60 (t, J=7.2 Hz, 2H, N-CH₂-CH₂CH₂); 3.09 (da+m, 3H, piper-2H_c, –6H_c and –4H); 4.13 (t, J=6.3 Hz, 2H, O-CH₂); 6.83 (d, J=2.1 Hz, 1H, 8H); 6.95 (dd, J=9 and 2.1 Hz, 1H, 6-H); 7.05 (td, J=8.7 and 2.1 Hz, 1H, benzisoxazole-5H); 7.25 (dd, J=8.7 and 2.1 Hz, 1H, benzisoxazole-7H); 7.69 (dd, J=8.7 and 4.8 Hz, 1H, benzisoxazole-4H); 7.71 (d, J=2.1 Hz, 1H, 2-H); 8.13 (d, J=9 Hz, 1H, 5-H).

IR (KBr): 1644, 1607, 1444, 1237 cm⁻¹.

Example 3

7-[3-[4-(6-fluoro-1,2-benzisoxazole-3-yl) piperidin-1-yl]propoxy]-3-(hydroxymethyl)-chromen-4-one By the procedure described above, starting from 2.0 g (7.5 mmoles) of 7-(3-chloropropoxy)-3-(hydroxymethyl) chromen-4-one and 1.93 g (7.5 mmoles) of 6-fluoro-3-(4-piperidinyl)-1,2-benzisoxazole hydrochloride, a solid was obtained by crystallization of the crude product from dimethylformamide to yield 1.27 g of 7-[3-[4-(6-fluoro-1,2-benzisoxazole-3-yl)piperidin-1-yl]propoxy]-3-(hydroxymethyl)-chromen-4-one, mp 200°–202° C.

¹H-NMR (CDCl₃+CD₃OD): δ=2.10–2.35 (m, 8H); 2.68 (t, J=7.5 Hz, 2H, N-CH₂-CH₂CH₂); 3.13–3.18 (da+m, 3H, piper-2H_c, –6H_c and 4H); 4.18 (t, J=6.3 Hz, 2H, O-CH₂); 4.57 (s, 2H, CH₂OH); 6.96 (d, J=2.7 Hz, 1H, 8H); 7.03 (dd, J=9 and 2.4 Hz, 1H, 6-H); 7.12 (td, J=9 and 2.1 Hz, 1H, benzisoxazole-5H); 7.29 (dd, J=8.7 and 2.1 Hz, 1H, benzisoxazole-7H); 7.53 (5, 1H, 2-H); 7.81 (dd, J=9 and 5 Hz, 1H, benzisoxazole-4H); 8.09 (d, J=9 Hz, 1H).

IR (KBr): 3300–3600, 1634, 1603, 1444, 1272, 1242 cm⁻¹.

Example 4

7-[3-[4-(6-fluoro-1,2-benzisoxazole-3-yl) piperidin-1-yl]propoxy]chromen-4-one hydrochloride 7-[3-[4-(6-fluoro-1,2-benzisoxazole-3-yl)piperidin-1-yl]propoxy]chromen-4-one hydrochloride was obtained by adding the stoichiometric quantity of aqueous hydrochloric acid over a solution of the base in acetone. The solid which precipitated was recrystallized from methanol to give 7-[3-]4-(6-fluoro-1,2-benzisoxazole-3-il)piperidin-1-yl]propoxy]chromen-4-one, mp 260°–262° C.

H¹-NMR (CD₃OD+D₂O): δ=2.2–2,4, m, 8H; 2.59, t, 2H; 3.19–3.4, m, 5H; 6.34, d, 1H; 7.13, d, 1H; 7.15–7.19, dd, 1H; 7.28–7.36, dr, 1H; 7.60–7.64, dd, 1H; 7.09–8.04, m, 2H; 8.20, d, 1H.

IR (KBr): 1705, 1660, 1450, 1275, 845, 825 cm⁻¹.

Example 5

Injection formulation.

Composition for 1 ampoule:

| | |
|---|---|
| 7-[3-[4-(6-fluoro-1,2-benzisoxazole-3-yl) piperidin-1-yl]propoxy]chromen-4-one | 5.0 mg |
| Methyl p-hydroxybenzoate | 1.0 mg |
| Propyl p-hydroxybenzoate | 0.1 mg |
| Bidistilled water q.s. | 2.0 ml |

Example 6

1% oral solution formulation

| | |
|---|---|
| 7-[3-[4-(6-fluoro-1,2-benzisoxazole-3-yl) piperidin-1-yl]propoxy]chromen-4-one | 1000 mg |
| methyl p-hidroxibenzoato | 135 mg |
| propyl p-hidroxibenzoato | 15 mg |
| Sorbitol 70% | 20 g |
| Sodium saccharin | 50 mg |
| Orange essence | 0.25 ml |
| Distilled water q.s. | 100 ml |

Example 7

Tablet formulation

Composition for 10 mg tablet:

| | |
|---|---|
| 7-[3-[4-(6-fluoro-1,2-benzisoxazole-3-yl) piperidin-1-yl]propoxy]chromen-4-one | 10.0 mg |
| Corn starch | 43.2 mg |
| Talc | 6.0 mg |
| Hydrogenated castor oil | 2.0 mg |
| Lactose q.s. | 200.0 mg |

Example 8

Tablet formulation

Composition for 50 mg tablet:

| | |
|---|---|
| 7-[3-[4-(6-fluoro-1,2-benzisoxazole-3-yl) piperidin-1-yl]propoxy]chromen-4-one | 50.0 mg |
| Corn starch | 86.4 mg |
| Talc | 12.0 mg |
| Hydrogenated castor oil | 4.0 mg |
| Lactose q.s. | 400.0 mg |

Example 9

7-[3-[4-(6-fluoro-1,2-benzisoxazole-3-yl) piperidin-1-yl]propoxy]-3-(hydroxymethyl)-chromen-4-one hydrochloride 7-[3-[4-(6-Fluoro-1,2-benzisoxazole-3-yl)piperidin-1-yl]propoxy]-3-(hydroxymethyl)-chromen-4-one hydrochloride was obtained by adding the stoichiometric amount of aqueous hydrochloric acid on the base dissolved in methanol, mp 244°–246° C.

IR (KBr): 3200–3600, 2500–2750, 1640, 1607, 1445, 1274, 1240 cm⁻¹.

Example 10

Injection formulation.

Composition for 1 ampoule:

| | |
|---|---|
| 7-[3-[4-(6-fluoro-1,2-benzisoxazole-3-yl)piperidin-1-yl]propoxy]-3-(hydroxymethyl)-chromen-4-one | 0.5 mg |
| Methyl p-hydroxybenzoate | 1.0 mg |
| Propyl p-hydroxybenzoate | 0.1 mg |
| Bidistilled water q.s. | 2.0 ml |

Example 11

0.1% oral solution formulation

| | |
|---|---|
| 7-[3-[4-(6-fluoro-1,2-benzisoxazole-3-yl)piperidin-1-yl]propoxy]-3-(hydroxymethyl)-chromen-4-one | 100 mg |
| Methyl p-hydroxybenzoate | 135 mg |
| Propyl p-hydroxybenzoate | 15 mg |
| Sorbitol 70% | 20 g |
| Sodium saccharin | 50 mg |
| Orange essence | 0.25 ml |
| Distilled water q.s. | 100 ml |

Example 12

Tablet formulation
Composition for 1 mg tablet:

| | |
|---|---|
| 7-[3-[4-(6-fluoro-1,2-benzisoxazole-3-yl)piperidin-1-yl]propoxy]-3-(hydroxymethyl)-chromen-4-one | 1.0 mg |
| Corn starch | 32.4 mg |
| Talc | 4.5 mg |
| Hydrogenated castor oil | 1.5 mg |
| Lactose q.s. | 150.0 mg |

Example 13

Tablet formulation
Composition for 5 mg tablet:

| | |
|---|---|
| 7-[3-[4-(6-fluoro-1,2-benzisoxazole-3-il)piperidin-1-yl]propoxy]-3-(hydroxymethyl)-chromen-4-one | 5.0 mg |
| Corn starch | 43.2 mg |
| Talc | 6.0 mg |
| Hydrogenated castor oil | 2.0 mg |
| Lactose q.s. | 200.0 mg |

We claim:

1. 4-(6-fluoro-1,2-benzisoxazolyl)-1-piperidinyl-propoxy-chromen-4-one derivatives of formula (I):

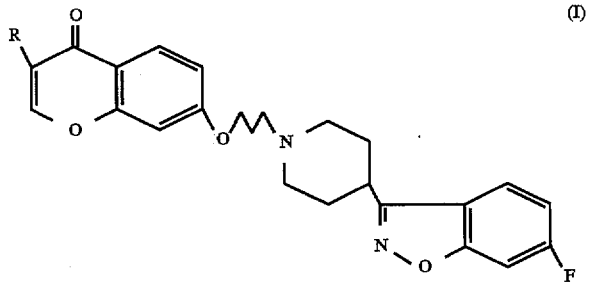

wherein R is hydrogen or alkyl having 1 to 4 carbon atoms optionally substituted by hydroxyl, or a pharmaceutically acceptable addition salt thereof.

2. The compound according to claim 1, which is selected from the group consisting of: 7-[3-[4-(6-fluoro-1,2-benzisoxazole-3-yl)piperidin-1-yl]propoxy]chromen-4-one; 7-[3-[4-(6-fluoro-1,2-benzisoxazole-3-yl)piperidin-1-yl]propoxy]-3-methyl-chromen-4-one; and 7-[3-[4-(6-fluoro-1,2-benzisoxazole-3-yl)piperidin-1-yl]propoxy]-3-(hydroxymethyl)-chromen-4-one; or a pharmaceutically acceptable addition salt thereof.

3. A pharmaceutical composition comprising a compound of formula (I) according to claim 1, or a pharmaceutically acceptable addition salt thereof, and a pharmaceutically acceptable carrier.

4. A method for the treatment of psychosis, schizophrenia or anxiety which comprises administering to a mammal an effective amount of a compound of formula (I) according to claim 1, or a pharmaceutically acceptable addition salt thereof.

5. A process for preparing a compound of formula (I) according to claim 1 which comprises reacting a 7-(3-halopropoxy)-4H-1-benzopyran-4-one of general formula (II):

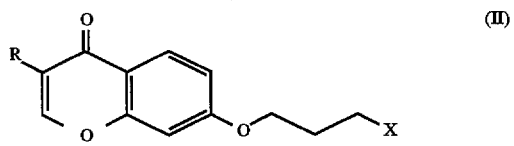

wherein R is as defined for (I) and X is chlorine or bromine, with 6-fluoro-3-(4-piperidinyl)-1-2-benzisoxazole of formula (III):

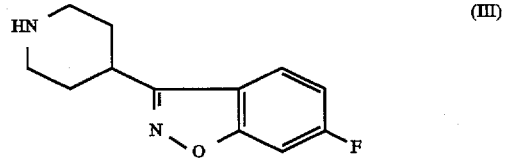

and optionally, converting the compounds of claim 1 in free base form into an acid addition salt thereof.

6. The method according to claim 4, for treating anxiety.

7. The method according to claim 4, for treating schizophrenia.

* * * * *

UNITED STATES PATENT AND TRADEMARK OFFICE
CERTIFICATE OF CORRECTION

PATENT NO. : 5,736,558
DATED : April 7, 1998
INVENTOR(S) : Foguet, et. al.

It is certified that error appears in the above-indentified patent and that said Letters Patent is hereby corrected as shown below:

Title page, item [54] and col. 1, in the Title, change:

"4-(6-FLUORO-1,2-BENZISOXAZOLYL)-1-PIPERIDINYL-PROPOXY-CHROMEN-4-ONE-ONE-DERIVATIVES, THEIR PREPARATION AND THEIR USE IN THE TREATMENT OF PSYCHOSIS, SCHIZOPHRENIA AND ANXIETY"

to

--4-(6-FLUORO-1,2-BENZISOXAZOLYL)-1-PIPERIDINYL-PROPOXY-CHROMEN-4-ONE-DERIVATIVES, THEIR PREPARATION AND THEIR USE IN THE TREATMENT OF PSYCHOSIS, SCHIZOPHRENIA AND ANXIETY--

Signed and Sealed this

Fourth Day of August, 1998

Attest:

*Attesting Officer*

BRUCE LEHMAN

*Commissioner of Patents and Trademarks*